United States Patent [19]

Stevenson et al.

[11] Patent Number: 5,364,895
[45] Date of Patent: Nov. 15, 1994

[54] HYDROLYTICALLY STABLE PENTAERYTHRITOL DIPHOSPHITES

[75] Inventors: Donald R. Stevenson; Duong N. Nguyen, both of Dover; Arthur W. McRowe, Bart, all of Ohio

[73] Assignee: Dover Chemical Corp., Dover, Ohio

[21] Appl. No.: 108,658

[22] PCT Filed: Jan. 20, 1993

[86] PCT No.: PCT/US93/00499
§ 371 Date: Aug 30, 1993
§ 102(e) Date: Aug 30, 1993

[87] PCT Pub. No.: WO94/17082
PCT Pub. Date: Aug. 4, 1994

[51] Int. Cl.$^5$ .................. C08K 5/527; C07F 9/6578
[52] U.S. Cl. .................................................. 524/120
[58] Field of Search ........................ 558/78; 524/120

[56] References Cited

U.S. PATENT DOCUMENTS

| | | | |
|---|---|---|---|
| 2,847,443 | 8/1958 | Hechenbleikner | 260/461 |
| 3,192,243 | 6/1965 | Gagliani | 260/461 |
| 3,205,250 | 9/1965 | Hechenbleikner | 260/461 |
| 3,845,142 | 10/1974 | Gurvich | 260/619 |
| 4,064,100 | 12/1977 | Hechenbleikner | 260/45.8 |
| 4,064,101 | 12/1977 | Mark . | |
| 4,066,611 | 1/1978 | Cooper et al. . | |
| 4,116,926 | 9/1978 | York | 260/967 |
| 4,116,939 | 9/1978 | Axelrod . | |
| 4,206,111 | 6/1980 | Valdiserri et al. . | |
| 4,259,534 | 3/1981 | Gurvich et al. | 568/720 |
| 4,261,880 | 4/1981 | Fujii et al. | 260/45.8 |
| 4,290,976 | 9/1981 | Hechenbleikner et al. . | |
| 4,299,885 | 11/1981 | Sahajpal et al. . | |
| 4,305,866 | 12/1981 | York et al. | 260/45.7 |
| 4,331,585 | 5/1982 | Valdiserri et al. . | |
| 4,385,145 | 5/1983 | Horn . | |
| 4,403,053 | 9/1983 | Lewis . | |
| 4,413,078 | 11/1983 | Lewis et al. . | |
| 4,492,661 | 6/1985 | Maul et al. | 260/967 |
| 4,588,764 | 5/1986 | Lee . | |
| 4,665,221 | 5/1987 | Marlin et al. | 558/28 |
| 4,754,077 | 6/1988 | Mina | 568/720 |
| 4,855,345 | 8/1989 | Rosenberger et al. | 524/120 |
| 4,912,198 | 3/1990 | Fontana . | |
| 4,983,657 | 1/1991 | Humplik et al. | 524/120 |
| 5,137,950 | 8/1992 | Hobbs et al. | 524/120 |

FOREIGN PATENT DOCUMENTS

| | | | |
|---|---|---|---|
| 199997 | 5/1991 | European Pat. Off. . | |
| 2156358 | 10/1985 | United Kingdom | 558/78 |

*Primary Examiner*—Veronica P. Hoke
*Attorney, Agent, or Firm*—Oldham, Oldham & Wilson

[57] ABSTRACT

A class of hydrolytically stable bis(aralkylphenyl)pentaerythritol diphosphites is disclosed, which is suitable as an antioxidant additives in polyolefins, particularly, in polypropylene. The diphosphites are of low volatility, have a high thermal decomposition temperature and resist yellowing when blended into a polyolefin base. A preferred diphosphite is bis(2,4-dicumylphenyl)pentaerythritol diphosphite.

13 Claims, No Drawings

HYDROLYTICALLY STABLE PENTAERYTHRITOL DIPHOSPHITES

TECHNICAL FIELD

The invention described herein pertains generally to a new class of phosphites, i.e., a bis(aralkylphenyl)pentaerythritol diphosphites, and their ability to be used as a stabilizer for several polymers, particularly, polypropylene.

BACKGROUND OF THE INVENTION

Plastics are used in a myriad of widely diverse applications, in automobile parts, in components for houses and buildings, and in packaging from food to electronic parts. Plastics would not be able to perform such diverse functions without the assistance of a very broad range of plastics additives. Without them, some plastics would degrade during processing and, over time, the polymers would lose impact strength, discolor, and become statically charged, to list just a few problems. Additives not only overcome these and other limitations, but also can impart improved performance properties to the final product.

Formulating with plastics additives has always been a tricky business. Incorporating additives into a polymer requires a fine balance between the properties of the polymer and the additive. Formulating a plastic for enhanced ultraviolet light resistance, for example, can have an impact on the polymer's color stability and retention of its functional characteristics. Formulators need to choose additives carefully, so that the additive not only possesses a specific functionality, but that it also minimizes the effect on other additives and the formulated plastic.

Antioxidants are but one class of additives applicable in polyolefin and other polymer resins. These additives retard the oxidative degradation of a plastic. Degradation is initiated when free radicals, (highly reactive species with an unpaired electron), are created in the polymer by heat, ultraviolet radiation, mechanical shear, or metallic impurities. Without the protection of antioxidants, loss of molecular weight, brittleness, discoloration, crosslinking, and deterioration of other polymer properties will occur.

When a free radical is formed, a chain reaction begins that initiates polymeric oxidation. Subsequent reaction of the radical with an oxygen molecule yields a peroxy radical, which then reacts with an available hydrogen atom to form an unstable hydroperoxide and another free radical. In the absence of an antioxidant, these reactions become self-propagating, and lead to polymer degradation.

There are two basic types of antioxidants, primary and secondary. Primary antioxidants intercept and stabilize free radicals by donating active hydrogen atoms. Hindered phenols and aromatic amines represent the two main types of primary antioxidants. Secondary antioxidants prevent formatin of additional free radicals by decomposing the unstable hydroperoxides into a stable product. Phosphites and thioesters are secondary antioxidants that function by decomposing hydroperoxides, thus preventing free-radical formation. Secondary antioxidants are often used along with primary antioxidants, but can be used alone, especially if they contain a hindered phenolic group within their structure. Together they decrease the discoloration of the polymer and may also regenerate the primary antioxidant.

There are several commercially available phosphites that are used to stabilize polymer materials against color degradation and melt flow degradation. One product which has been found to be especially useful is a bis(2,4-di-t-butylphenyl)pentaerythritol diphosphite as shown by formula (I) described in U.S. Pat. No. 4,305,866 to York.

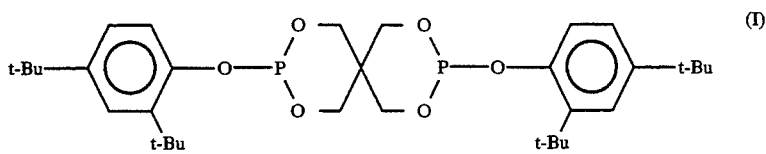

Another product which has been mentioned in the literature is bis(2-t-butyl-4-{alpha,alpha'-dimethylbenzyl})pentaerythritol diphosphite as shown by formula (II), described in U.S. Pat. No. 4,983,657 to Humplik.

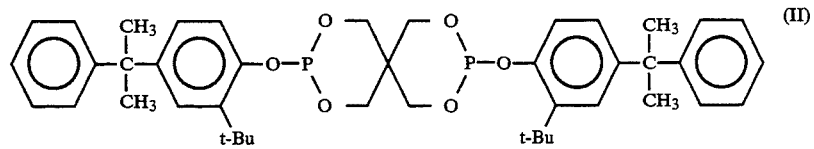

Both phosphites of formulas (I) and (II) have problems in that they are hygroscopic, and are not hydrolytically stable. On exposure to moisture for a period of time, they have a tendency to lump and become a sticky mass.

Additionally, symmetrical triarylphosphite stabilization systems have been described for polyolefins in U.S. Pat. No. 4,187,212 to Zinke et al., as shown for example in formula (III)

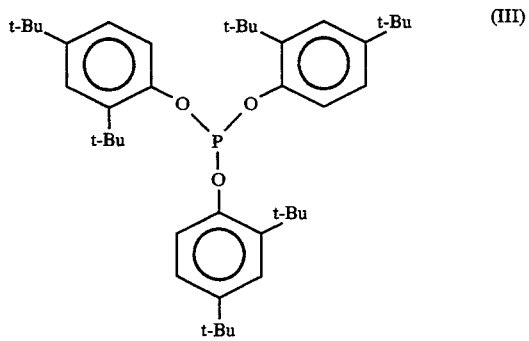

While this phosphite does possess good hydrolytic stability, it is not as effective as desired for color stability and melt-flow stabilization. Pentaerythritol diphosphites such as shown in formulas (I) and (II) are more effective in maintaining color stability.

To date, there still exists a need to provide a phosphite product, based on pentaerythritol, which is slower to absorb moisture, thereby maintaining its effectiveness for longer periods of time in humid conditions.

SUMMARY OF THE INVENTION

In accordance with the present invention, there is provided more hydrolytically stable bis(aralkylphenyl)-pentaerythritol diphosphites, which are suitable as an antioxidant additive in polyolefins, particularly, in polypropylene.

It is an object of this invention to provide a thermally stable polymer additive of low volatility, which possesses a high thermal decomposition temperature.

It is another object of this invention to provide a polymer additive which is resistant to phosphite hydrolysis upon exposure to moisture for an extended period of time, thereby remaining granular and free-flowing.

It is still another object of this invention to maintain the Hunter yellowness color index number as low as possible thereby indicating that the additive has limited the amount of degradation of the polymer under processing conditions.

It is yet another object of this invention to maintain the melt-flow index of the polymer thereby indicating that the additive has limited the amount of degradation of the polymer under processing conditions.

It is a further object of this invention to provide a method for synthesizing a bis(aralkylphenyl)pentaerythritol diphosphite in improved yield.

It is yet a further object of this invention to demonstrate that a bis(aralkylphenyl)pentaerythritol diphosphite can be used in combination with a class of hindered phenols to maintain both color and minimize melt-degradation of the polymer in a synergistic manner.

conditions: polymer drying; polymer pelletizing and compounding; polymer storage and shipment; polymer fabrication processing; and during recycling.

One technique which ameliorates some of the above problems is through the use of an additive, in particular, a phosphite additive. One of the problems with the addition of pentaerythritol phosphite stabilizers has been their tendency to absorb moisture, thereby decreasing the product's ability to flow freely. It has been found, that pentaerythritol-based diphosphites of the invention, shown in generic form as formula (IV), are more hydrolytically stable than prior art pentaerythritol diphosphites, and therefore require less precautions to be taken in their handling, and are more desirable as additives.

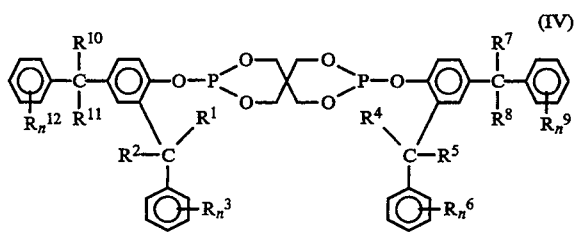

Specifically, within the pentaerythritol-based diphosphite of formula (IV), $R^1$, $R^2$, $R^3$, $R^4$, $R^5$, $R^7$, $R^8$, $R^{10}$ and $R^{11}$ are selected independently from the group consisting of hydrogen, alkyl radicals of generic formula $C_mH_{2m+1}$ wherein m ranges from 1 to 4 and substituted derivatives thereof; $R_n^3$, $R_n^6$, $R_n^9$, and $R_n^{12}$ are selected independently from the group consisting of hydrogen, alkyl radicals of generic formula $C_mH_{2m+1}$ wherein m ranges from 1 to 4, aryl radicals, and further wherein n ranges from 0 to 3, and the substituent is located at a position ortho, meta or para to the bridging methylene radical.

In particular, a preferred embodiment of the invention, is a diphosphite of formula (V), a bis(2,4-dicumylphenyl)pentaerythritol diphosphite.

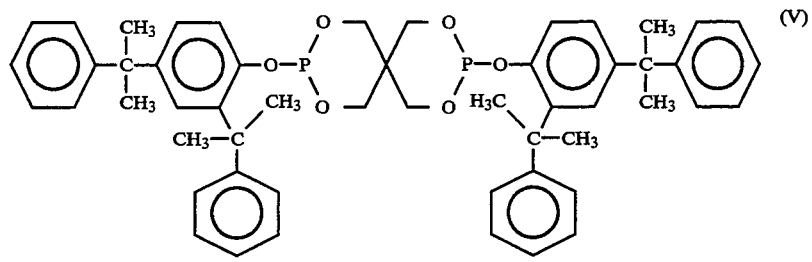

These and other objects of this invention will be evident when viewed in light of the detailed description and appended claims.

DETAILED DESCRIPTION OF THE INVENTION

Polymer degradation is the deterioration in the physical properties of a polymer caused by chemical reactions involving the backbone of the polymer chain. Symptoms of degradation are yellowing, loss of tensile strength, loss of impact strength, changes in melt-flow, and poor processability. This degradation can be caused by contamination in the polymer, residual catalyst (potentially causing depolymerization), temperature, and light. Degradation tends to occur under the following Cost and time prohibit real-life testing of stabilizer systems, therefore laboratory tests have been developed to simulate conditions under which degradation occurs. Thermal gravimetric analysis (TGA) is a sensitive technique used to follow the weight change of a sample as a function of temperature, thereby providing information about the thermal stability, volatiity and decomposition temperature temperature of the material studied. The test simulates conditions which the polymer would experience during manufacturing and compounding.

As shown in Table I, TGA scans were used to measure the thermal stability of a series of phosphite stabilizers shown previously by formulas (I), (II), (III) and (V). The percentage weight loss of the starting phosphite was determined as a function of temperature.

TABLE I

| | TGA[1] Comparison | | | |
|---|---|---|---|---|
| | temperature at % of weight loss | | | |
| Percent weight loss | T(°C.) Phosphite (I) | T(°C.) (III) | T(°C.) (V) | T(°C.) (II) |
| 5 | 250 | 258 | 250 | 314 |
| 10 | 275 | 265 | 275 | 332 |
| 20 | 300 | 282 | 300 | 343 |
| 30 | 315 | 293 | 318 | 350 |
| 40 | 320 | 297 | 329 | 354 |
| 50 | 327 | 303 | 336 | 365 |
| 80 | 345 | 318 | 364 | 375 |

[1]DuPont 2000 TGA using a heating rate of 10° C. from room temperature to 800° C. under nitrogen As shown in Table I, the bis(2,4-dicumylphenyl)pentaerythritol diphosphite (V) exhibited good high temperature stability and low volatility in comparison to the bis(2,4-di-t-butylphenyl)pentaerythritol diphosphite of formula (I) and the trisubstituted symmetrical triphenylphosphite of formula (III) and similar characteristics to the bis(2-t-butyl-4-{$\alpha,\alpha'$-dimethylbenzyl})pentaerythritol diphosphite of formula (II).

All phosphites will eventually react with water and hydrolyze. As this reaction occurs, an acidic species is produced which is titratable. In the first stage of hydrolysis, the phosphite reacts with a molecule of water to form an alcohol or substituted phenol and dialkyl or dialkylaryl phosphite. The dialkyl or dialkylaryl phosphite once again reacts with water to form a monoester and once more with water to yield the dibasic phosphorous acid. By monitoring a phosphite for the alcohol or phenol and acid content, the extent of hydrolysis can be determined and thereby gauge the product's fitness for use.

The acid number was determined by weighing out a one gram phosphite sample. Approximately 75 ml of methylchloride was neutralized with 0.02N sodium butylate to a blue-green endpoint using about 4-6 drops of a 0.1% bromothymol blue indicator solution. The neutralized methylene chloride was added to the phosphite sample and dissolved. The solution was immediately titrated with 0.02N sodium butylate to a blue-green endpoint.

A hydrolytic stability comparison was made between the prior art products, formulas (I) and (II) in comparison to new formula (V), by exposing the 5 g samples of the phosphites to 85% relative humidity at about 25° C. for various periods of time, and noting when the powder changed its physical characteristics to either non-powdery or became sticky and lumpy. Without being held to any particular theory, it is proposed that the hydrolytical stability of formula (V) is due to the large bulky groups adjacent to the phosphorus. This provides a good deal of steric hindrance to hydrolysis.

TABLE II

| | Phosphite Hydrolysis[1] | | | |
|---|---|---|---|---|
| Hours | 0 | 67 | 163 | consistency after 163 hrs |
| Phosphite | acid number[2] | | | |
| (I) | 0.06 | 0.01 | 21.9 | sticky |
| (II) | 0.08 | 0.12 | 10.1 | sticky |
| (V) | 0.67 | 2.36 | 6.13 | granular & free flowing |

[1]exposure phosphites to 85% relative humidity at 25° C.
[2]acid number (mg KOH/g) as a function of time (hours)

As can be seen in Table II, diphosphites of formulas (II) and (V) exhibit a lower acid number for longer periods of time, and additionally, for the case of formula (V), the diphosphite remains granular and free-flowing even after exposure to extremely elevated moisture levels for more than 163 hours.

Tests which simulate compounding and fabrication include measurements of the polymers' torque rheometry using a Brabender and multiple pass extrusions. These tests subject the molten polymer to heat and shear for extended periods of time. After the test exposure, the polymer is prepared into samples which can be used for physical property, color, and viscosity testing. A Brabender plasticorder PL2000, multipurpose instrument was used to study the viscosity or flow properties of polymer materials under various temperatures and shear rates. For testing, samples were prepared by accurately weighing additives to be added to the polymer (e.g., polypropylene). They were dry blended in a plastic 1000 ml beaker by shaking for approximately 5 minutes.

The Brabender consisted essentially of a measuring head with roller blades, drive control and measuring unit. For the series of tests performed, the temperature was set at 200° C. and the speed was 100 rpm. The sample weight was 39 g. The length of the time of the test was approximately 12-40 minutes. The sample to be evaluated was charged to the mixer head by means of a loading chute ram on a 5 kg weight. The Brabender then continuously recorded torque, which is a measure of viscosity at a constant temperature of 200° C. over a time period varying from 0-40 minutes. Torque and temperature were continuously monitored. Torque gives an indication of the viscosity of the polymer. For polypropylene, as the polymer degrades, the viscosity decreases and the torque decreases. Immediately upon conclusion of the test, the measuring head was removed. Using a brass knife, a sample was quickly removed to be used for color determination from the mixing head and placed on a clean stainless steel plate. The sample was measured for color determination. When cool, the sample was placed between two polished plates and inserted in a Carver press for 6 minutes at 5 metric tons of pressure and a temperature of about 150° C. After pressing the plates containing the samples, they were cooled for 6 minutes, the sample removed and the color read on a Hunter Colorimeter. The Brabender also computed the specific energy imparted to the sample over the period of time the evaluation was carried out. The higher the specific energy for a given period of time, the less the polymer degraded.

Melt indexes were measured in accordance with the requirements of Condition L of ASTM D1238. The test method covers measurement of the rate of exudation of molten resin through a die of a specified length and diameter under prescribed conditions of temperature and load. The results of this test give some indication of the molecular weight of the polymer. For polypropylene, as the polymer is degraded and the molecular weight decreases, the melt index or flow through the orifice increases. For Condition L, the temperature is 230° C. with a load of 2.16 kg. Melt index or melt flow is given in numbers of g/10 minutes.

Color measurements were determined using a Hunter Lab D25-PC2 Delta Processor. This processor calculates the yellowness index per ASTM D1925 and ASTM E313. The industrial standard for measuring color for polymer such as polyethylene and polypropylene is the yellowness index. Visually, yellowness can be associated with scorching, soiling and general product degradation by light, chemical exposure or processing variables. Yellowness Index, ASTM D1925 is used to measure these types of degradation for plastics and paint industries. The test is carried out by comparing the yellowing of the sample to a white standard the lower the number YI, the whiter the sample and the less degradation. The higher the YI, the yellower the sample and indicates more degradation.

Typically polymers such as polypropylene, polystyrene, polyethylene terephthalates (PET), polyalkylene terephthates, and polycarbonates will tend to break down or chain scission as they are processed at higher temperatures for a period of time. This will result in an increase in melt index. Polyethylene on the other hand, can increase in molecular weight due to crosslinking and oxidation. When evaluating polyethylene by melt index, and basically for all polymers, it is desirable that the melt index not change from the beginning to the end.

In regard to the yellowness index, the more the polymer is processed, the higher the yellowness index or the darker the material becomes. Again, it is desirable that there be minimal change in this index during processing.

TABLE III

Evaluation of Phosphites in Polypropylene

| Polymer composition | Torque[3] (meter-grams) | | | Hunter YI yellowish color index |
|---|---|---|---|---|
| | 12 min | 24 min | 36 min | |
| base[1] | 875 | 550 | 375 | 40.8 |
| base + (I)[1] | 1075 | 720 | 395 | 17.5 |
| base + (II)[2] | 1025 | 700 | 375 | 17.6 |
| base + (V)[2] | 1075 | 725 | 375 | 15.5 |
| base + (III)[2] | 1000 | 685 | 375 | 44.3 |

[1]base formulation
(a) 100 parts polypropylene, Profax TM 6501 produced by Himont, an isotactic homopolymer with a melt-index of 4, a density of 0.9 g/cm³, a tensile strength of 5,000 psi, and elongation at yield of 12%.
(b) 0.10 parts Irganox 1076 (octadecyl 3-(3',5-di-t-butyl-4'-hydroxyphenyl)propionate, formula (VI))

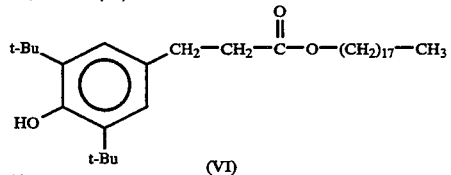

(VI)

[2]0.2% phosphites added to the base
[3]Brabender temperature 200° C. - 100 rpm

As shown in Table III, without the addition of any phosphite additive, the torque, which is a measure of the polymer degradation, measured at 12 min. was significantly lower than the torque measured for samples to which 0.2% phosphites had been added. Additionally, the unstabilized polypropylene exhibited significant discoloration as indicated by the high yellowish color index number. The diphosphite (V) performed equally effectively to that of a known state-of-the-art products, formulas (I) and (III), and significantly better than formula (III) in discoloration.

The improvement resides therefore, in the ability to outperform phosphites, such as formula (I) and (II) in its resistance to hydrolysis, as indicated in Table (II) and additionally, in its inherent thermal stability as indicated in Table (I).

A multi-extrusion study was performed using phosphite (V), a bis-2,4-dicumylpentaerythritol diphosphite, with several other phosphites using polypropylene in accordance with the amounts shown in Table IV. The samples were blended and extruded at 210° C. through a twin-screw extruder. The extruded material was pelletized and a small sample was retained for melt-flow and color resting. The remaining pellets were extruded again, up to a total of five extrusions.

TABLE IV

Multi-Pass Extrusion Study

| base[1] polymer | Additives | | | melt flow[5] 1st pass | melt flow[5] 5th pass | YI[6] 1st pass | YI[6] 5th pass |
|---|---|---|---|---|---|---|---|
| | Ca[2] | phenol[3] | phosphite[4] | | | | |
| #1 PP | 0.05% | 0% | 0% | 26.9 | 208.3 | 4.6 | 6.7 |
| #2 PP | | 0.1% | 0% | 7.0 | 12.2 | 4.5 | 6.3 |
| #3 PP | | 0.1% | (V) 0.05% | 5.9 | 7.8 | 4.5 | 5.4 |
| #4 PP | | 0.1% | (I) 0.05% | 3.9 | 4.8 | 4.0 | 6.1 |
| #5 PP | | 0.1% | (II) 0.05% | 3.5 | 4.8 | 4.0 | 6.1 |
| #6 PP | | 0.1% | (III) 0.05% | 6.0 | 54.6 | 4.3 | 5.4 |
| #7 PP | | 0.1% | (V) 0.05% | 4.0 | 5.1 | 4.0 | 4.6 |
| #8 PP | | 0.05% | (V) 0.10% | 3.9 | 15.0 | 4.1 | 4.4 |

[1]polypropylene (PP)
[2]calcium stearate
[3]hindered phenol (I-1076 of formula (VI))
[4]amount of added phosphite of appropriate formula
[5]melt flow (grams/10 minutes)
[6]Hunter Yellowness Color Index The data clearly shows that the phosphite of formula (V) does improve the stability over the base polymer. Additionally, as shown in run #8, it is also indicated that doubling the level of phosphite (V), does indicate that less of the polymer is degraded. The amount of phosphite added is well-known by those skilled in the art, but in general is guided by cost considerations and FDA approval. Typical amounts added however, will generally range from 0.01% to about 0.5%.

While only one hindered phenol is shown in Table IV, there are many different phenolic compounds which are equally suitable for use in the invention, and well-known to those skilled in the art. A non-inclusive list of examples of such suitable phenolic-based compounds would be: Bisphenol TM A (Dow Chemical Co., 4,4-isopropylidene-diphenol); TENOX TM BHA (Eastman Chemical, butylated hydroxyanisole); ETHANOX TM 330 (Ethyl Corp., 1,3,5-trimethyl-2,4,6-tris(3,5-di-di-tert-butyl-4-hydroxybenzyl)benzene); ETHANOX TM 702 (Ethyl Corp., 4,4-methylene-bis(2,6-di-tert-butylphenol)); MIXXIM TM AO-30 (Fairmount Chemical Co., 1,1,3-tris(2-methyl-4-hydroxy-5-tert-butylphenyl)butane); ANULLEX TM BHEB, (Hodgson Chemicals Ltd., 2,6-di-tert-butyl-4-ethylphenol); HOSTANOX TM 03 (Hoechst Celanese Corp., bis-[3,3-bis-(4'-hydroxy-3-tert-butyl-phenyl-butanoic acid]-glycol ester)); TOPANOL TM CA (ICI Americas Inc., 1,1,3-tris(2-methyl-4-hydroxy-5-tert-butyl-phenyl)butane); SANTONOX TM R (Monsanto Co., 4,4-thio-bis(6-tert-butyl-m-cresol)); SANTONOX ™ (Monsanto Co., 4,4-thio-bis(2-tert-butyl-m-cresol)); SANTOWHITE (Monsanto Co., 4,4′-butylidene-bis(2-tert-butyl-m-cresol)); SUSTANE BHT (UOP Biological & Food Products, 2,6-di-tert-butyl-p-cresol); VANOX ™ 1320 (R.T. Vanderbilt Co., Inc., 2,6-di-tert-butyl-4-sec-butylphenol); CYANOX ™ 425 (American Cyanamid Co., 2,2′-methylene-bis(4-ethyl-6-tert-butylphenol)); CYANOX 1790 (American Cyanamid Co., 1,3,5-(4-tert-butyl-3-hydroxy-2,6-dimethylbenzyl)-1,3,5-triazine-2,4,6-(1H,3H,5G)-trione); CYANOX ™ 2246 (American Cyanamid Co., 2,2-methylene-bis(4-methyl-6-tert-butylphenol)); IRGANOX ™ 245 (Ciba-Geigy Corp., 1,6-hexamethylene-bis(3,5-di-tert-butyl-4-hydroxyhydrocinnamate)); IRGANOX ™ 1010 (Ciba-Geigy Corp., tetrakis{methylene-3-(3,5-di-tert-butyl-4-hydroxyphenyl)propionate}methane); IRGANOX ™ 1076 (Ciba-Geigy Corp., octadecyl-3-(3′5-di-tert-butyl-4-hydroxyphenyl)propionate); IRGANOX 3114 (Ciba-Geigy Corp., 1,3,5-tris(3,5-di-tert-butyl-4-hydroxybenzyl)isocyanurate); and IRGANOX ™ 3125 (Ciba-Giegy Corp., 3,5-di-tert-butyl-4-hydroxyhydrocinnamic acid triester with 1,3,5-tris(2-hydroxyethyl)-s-triazine-2,4,6-(1H,3H,5H)trione).

EXAMPLES

The best mode for carrying out the invention will now be described for the purposes of illustrating the best mode known to the applicant at the time. The examples are illustrative only and not meant to limit the invention, as measured by the scope and spirit of the claims.

EXAMPLE 1

Preparation of bis(2,4-dicumylphenyl)pentaerythritol diphosphite of formula (V)

A glass reactor was fitted with an agitator, reflux condenser, and a gas outlet. The reactor was charged with 150 g of 2,4-dicumylphenol, 100 g heptane and 100 g toluene and heated to 35° C. After sufficient mixing, 62.6 g of PCl3 were added and the reaction mixture heated to 90° C. After 0.5 hours at 90°-95° C., HCl was still evolving. The reaction is allowed to proceed for approximately 1.25 hours at 90°-95° C., followed by cooling to 45° C. with the addition of 31.4 g of pentaerythritol under vigorous agitation. The reaction is allowed to proceed with agitation for about 3 hours at 50° C. A nitrogen purge was initiated over the reaction and 120 g of additional heptane was added to the batch with heating to 100° C. for 8 hours. The product is a milky-white suspension. After cooling, filtering and drying, 129 g of bis(2,4-dicumylphenyl)pentaerythritol diphosphite was recovered (66% yield). The acid number varied from 2 to 6. The mother liquor can be recycled into another batch to produce additional product if desired.

EXAMPLE 2

Preparation of bis(2,4-dicumylphenyl)pentaerythritol diphosphite of formula (V) with added trialkanolamine A glass reactor was fitted with an agitator, reflux condenser, and a gas outlet. The reactor was charged with 150 g of 2,4-dicumylphenol, 0.22 g of triethanolamine, 100 g heptane and 100 g toluene and heated to 35° C. After sufficient mixing, 62.6 g of PCl3 were added and the reaction mixture heated to 90° C. After 0.5 hours at 90°-95° C., HCl was still evolving. The reaction is allowed to proceed for approximately 1.25 hours at 90°-95° C., followed by cooling to 45° C. with the addition of 31.4 g of pentaerythritol under vigorous agitation. The reaction is allowed to proceed with agitation for about 3 hours at 50° C. A nitrogen purge was initiated over the reaction and 120 g of additional heptane was added to the batch with heating to 100° C. for 8 hours. The product is a milky-white suspension. After cooling, filtering and drying, 147 g of bis(2,4-dicumylphenyl)pentaerythritol diphosphite was recovered (75.4% yield). The acid number varied from 2 to 6. The mother liquor can be recycled into another batch to produce additional product if desired.

The addition of a trialkanol amine increasing the yield of bis(2,4-dicumylphenyl)pentaerythritol diphosphite from 66% to more than 75%.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A diphosphite of formula (IV) with improved resistance to hydrolysis and increased thermal stability comprising:

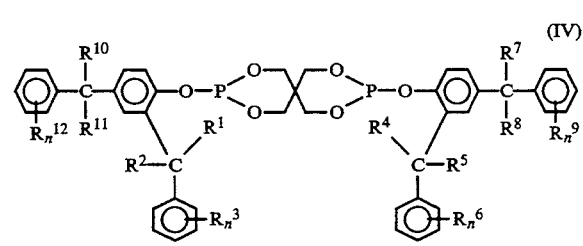

and wherein $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4 and $R^3$, $R^6$, $R^9$ and $R^{12}$ are selected independently from the group consisting of hydrogen and alkyl radicals of generic formula $C_mH_{2m+1}$ wherein m ranges from 1 to 4, and further wherein n ranges from 0 to 3.

2. The diphosphite of claim 1 wherein $R^1$, $R^2$, $R^4$, $R^5$, $R^6$, $R^7$, $R^8$, $R^{10}$, and $R^{11}$ are methyl radicals, and where n is 0 in $R_n^3$, $R_n^6$, $R_n^9$, and $R_n^{12}$ thereby forming a diphosphite of formula (V)

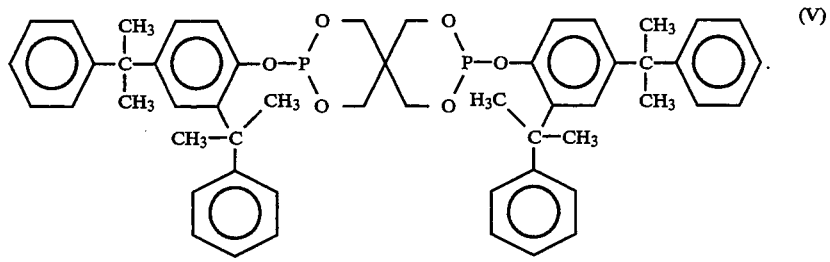

3. The diphosphite of claim 2 having an acid number of 6.13 or less after exposure to 85% relative humidity at 25° C. for 163 hours.

4. A polymer composition comprising
(a) a polyolefin; and
(b) a diphosphite sufficient to stabilize the polyolefin, the diphosphite of formula (IV)

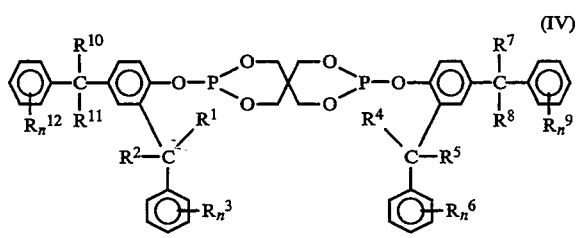

and wherein $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4 and $R^3$, $R^6$, $R^9$ and $R^{12}$ are selected independently from the group consisting of hydrogen and alkyl radicals of generic formula $C_mH_{2m+1}$ wherein m ranges from 1 to 4, and further wherein n ranges from 0 to 3.

5. The composition of claim 4 wherein $R^1$, $R^2$, $R^4$, $R^5$, $R^6$, $R^7$, $R^8$, $R^{10}$, and $R^{11}$ are methyl radicals, and where n is 0 in $R_n^3$, $R_n^6$, $R_n^9$, and $R_n^{12}$ thereby forming a diphosphite of formula (V)

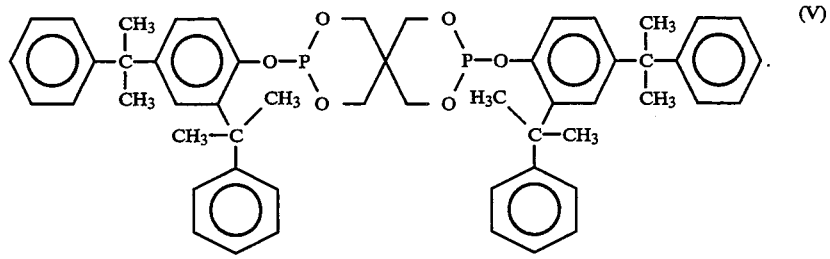

6. The polymer of claim 4 wherein the polyolefin is polypropylene.

7. A polymer composition comprising
(a) a polyolefin;
(b) a diphosphite sufficient to stabilize the polyolefin, the diphosphite of formula (IV)

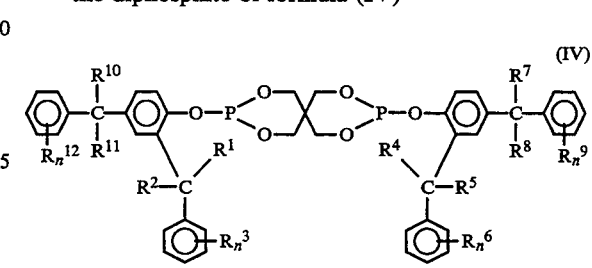

and wherein $R^1$, $R^2$, $R^4$, $R^5$, $R^7$, $R^8$, $R^{10}$ and $R^{11}$ are selected independently from the group consisting of hydrogen and alkyl radicals of generic formula $C_mH_{2m+1}$ wherein m ranges from 1 to 4 and $R^3$, $R^6$, $R^9$ and $R^{12}$ are selected independently from the group consisting of hydrogen and alkyl radicals of generic formula $C_mH_{2m+1}$ wherein m ranges from 1 to 4, and further wherein n ranges from 0 to 3; and
(c) a hindered phenol.

8. The composition of claim 7 wherein $R^1$, $R^2$, $R^4$, $R^5$, $R^6$, $R^7$, $R^8$, $R^{10}$, and $R^{11}$ are methyl radicals, and where n is 0 in $R_n^6$, $R_n^6$, $R_n^9$, and $R_n^{12}$ thereby forming a diphosphite of formula (V)

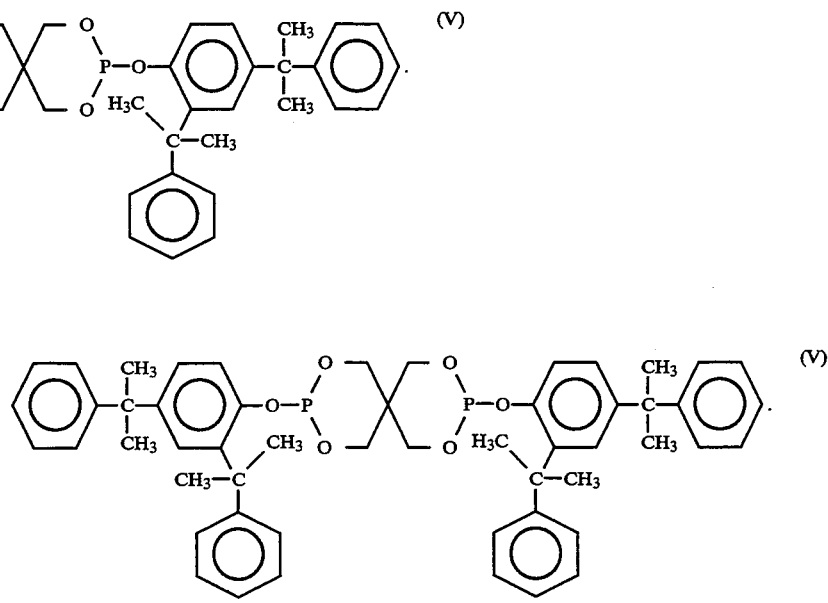

9. The polymer of claim 7 wherein the polyolefin is polypropylene.

10. The polymer of claim 7 wherein the hindered phenol is selected from the group consisting of 4,4'-isopropylidene-diphenol, butylated hydroxyanisole, 1,3,5-trimethyl-2,4,6-tris(3,5-di-di-tert-butyl-4-hydroxybenzyl)benzene, 4,4'-methylene-bis(2,6-di-tert-butyl-phenol), 1,1,3-tris(2-methyl-4-hydroxy-5-tert-butyl-phenyl)butane, 2,6-di-tert-butyl-4-ethylphenol, bis-[3,3-bis-(4'-hydroxy-3'-tert-butyl-phenyl-butanoic acid]-glycol ester, 1,1,3-tris(2-methyl-4-hydroxy-5-tert-butyl-phenyl)butane, 4,4'-thio-bis(6-tert-butyl-m-cresol), 4,4-thio-bis(2-tert-butyl-m-cresol), 4,4'-butylidene-bis(2-tert-butyl-m-cresol), 2,6-di-tert-butyl-p-cresol, 2,6-di-tert-butyl-4-sec-butylphenol, 2,2'-methylene-bis(4-ethyl-6-tert-butylphenol), 1,3,5-(4-tert-butyl-3-hydroxy-2,6-dimethylbenzyl)-1,3,5-triazine-2,4,6-(1H,3H,5G)-trione, 2,2'-methylene-bis(4-methyl-6-tert-butylphenol), 1,6-hexamethylene-bis(3,5-di-tert-butyl-4-hydroxyhydrocinnamate), tetrakis{methylene-3-(3,5-di-tert-butyl-4-hydroxyphenyl)propionate}methane, octadecyl-3-(3'5-di-tert-butyl-4-hydroxyphenyl)propionate, 1,3,5-tris(3,5-di-tert-butyl-4-hydroxybenzyl)isocyanurate, and 3,5-di-tert-butyl-4-hydroxyhydrocinnamic acid triester with 1,3,5-tris(2-hydroxyethyl)-s-triazine-2,4,6-(1H,3H,5H)trione.

11. The polymer of claim 10 wherein the hindered phenol is selected from the group consisting of tetrakis{methylene-3-(3,5-di-tert-butyl-4-hydroxyphenyl)propionate}methane, octadecyl-3-(3'5-di-tert-butyl-4-hydroxyphenyl)propionate, 1,3,5-tris(3,5-di-tert-butyl-4-hydroxybenzyl)isocyanurate, 3,5-di-tert-butyl-4-hydroxyhydrocinnamic acid triester with 1,3,5-tris(2-hydroxyethyl)-s-triazine-2,4,6-(1H,3H,5H)trione, 1,1,3-tris(2-methyl-4-hydroxy-5-tert-butyl-phenyl)butane, and 1,3,5-trimethyl-2,4,6-tris-(3,5-di-di-tert-butyl-4-hydroxybenzyl) benzene.

12. The polymer of claim 6 having an acid number of 6.13 or less after exposure to 85% relative humidity at 25° C. for 163 hours.

13. The polymer of claim 9 having an acid number of 6.13 or less after exposure to 85% relative humidity at 25° C. for 163 hours.

* * * * *